United States Patent [19]
Vemishetti et al.

[11] Patent Number: 5,476,938
[45] Date of Patent: Dec. 19, 1995

[54] PROCESS FOR THE PREPARATION OF NUCLEOTIDES

[75] Inventors: Purushortham Vemishetti; Paul R. Brodfuehrer; Henry G. Howell; Chester Sapino, Jr., all of Onondaga County, N.Y.

[73] Assignees: Institute of Organic Chemistry and Biochemistry of the Academy of Sciences of the Czech Republic, Czech Rep.; Rega Stichting v.z.w., Belgium

[21] Appl. No.: 822,271

[22] Filed: Jan. 21, 1992

Related U.S. Application Data

[63] Continuation of Ser. No. 566,200, Aug. 10, 1990, abandoned.

[51] Int. Cl.$^6$ ............................... C07F 9/38; C07F 9/40; C07B 43/00
[52] U.S. Cl. ............................. 544/243; 544/244
[58] Field of Search ....................... 544/243, 244

[56] References Cited

U.S. PATENT DOCUMENTS 4,808,716  2/1989  Holy et al. .............................. 544/244

FOREIGN PATENT DOCUMENTS 0253412  1/1988  European Pat. Off. ............... 544/243
2134907  8/1984  United Kingdom .

OTHER PUBLICATIONS

Kremzer Chem Abs 95, 132818a (1981).
Stevens, J Het Chem 20, 295 (1983).
Ueda, J Het Chem 8, 827 (1971).
Sata, Bull Chem Soc Japan 46, 1572 (1973).
Webb, Nucleosides & Nucleotides 8, 619 (1989).
Terry, Antiviral Res 10, 235–252 (1988).
Rosenberg, Coll. Czech Chem. Comm 53, 2753 (1988).
Robert M. Hanson, "The Synthetic Methodology of Nonracemic Glycidol and Related 2,3–Epoxy Alcohols", *Chemical Reviews*, vol. 91, No. 4, (Jun. 1991) pp. 437–475.

*Primary Examiner*—Mark L. Berch
*Attorney, Agent, or Firm*—Max D. Hensley

[57] ABSTRACT

The present invention relates to a novel and economical process for the synthesis of HPMP-substituted nucleotide antiviral compounds. Also disclosed are novel intermediates produced in the process for the preparation of HPMPC.

12 Claims, No Drawings

PROCESS FOR THE PREPARATION OF NUCLEOTIDES

This application is a continuation of Ser. No. 07/566,200, filed Aug. 10, 1990, now abandoned.

BACKGROUND OF THE INVENTION

1. Field of the Invention

The present invention relates to a novel process for the preparation of hydroxyphosphonylmethoxypropyl nucleosides, and novel intermediates produced therein.

2. Background Art

Nucleoside analogs possessing a 3-hydroxy-2-(phosphonylmethoxy)propyl (HPMP) side chain have been reported as potent antiviral compounds having a broad spectrum of activity. Examples of compounds belonging to this class include HPMP-adenine (HPMPA), HPMP-guanine (HPMPG) and HPMP-cytosine (HPMPC). HPMP-substituted nucleosides contain a chiral center and it has been postulated that the biological activity may reside in one enantiomer and not the other. It is therefore desirable to develop a synthetic method which will preferentially yield the active enantiomer using readily available and inexpensive starting materials.

Bronson et al (*J. Med. Chem.*, 1989, 32:1457) reported the synthesis of (S)-HPMPC which involves the coupling of cytosine with 3-O-benzyl-2-O-[(diethylphosphonyl)methyl]-3-O-(methylsulfonyl)glycerol, followed by subsequent deprotection to afford the product. The glycerol starting material is derived from chiral (R)-glycerol acetonide.

Holy et al (*Coll. Czech. Chem..Comm.*, 1989, 54:2470) reported the synthesis of (S)-HPMPC by reacting (R)-glycerol acetonide tosylate with 4-methoxy-2-pyrimidinone, the resultant product is then converted to 1-[(2,3-dihydroxy)propyl]cytosine. The latter compound is reacted with chloromethylphosphonyl dichloride, and the product is converted to (S)-HPMPC by base catalyzed rearrangement.

Glycerol acetonide was also used in the synthesis of (S)-HPMPA (Webb, Nucleosides and Nucleotides, 1989, 8:619) and HPMPG (Terry et al, *Antiviral Res.*, 1988, 10:235). These procedures all require the use of the expensive chiral glycerol acetonide as starting material, and involve multi-step process requiring chromatographic purifications of intermediate compounds.

The reaction of glycidol with adenine, cytosine or uracil to form the 2,3-dihyroxypropyl substituted nucleosides was reported by Ueda et al, *J. Heterocyclic Chem.*, 1971, 8:827. The reaction of (±)- glycidol with thymine or 5-fluorouracil was reported by Seiter et al, *Bull. Chem. Soc. Jpn.*, 1973, 46:1572. The prior art does not disclose or suggest the process of the present invention for the preparation of HPMP-nucleotides which offers marked improvement over previously known methods.

SUMMARY OF THE INVENTION

The present invention provides a novel and improved process for the preparation of hydroxyphosphonomethoxypropyl (HPMP) nucleoside antiviral compounds. The process of the instant invention comprises the steps of reacting an optionally substituted purine or pyrimidine base with an optionally substituted glycidol; if glycidol is used in the previous step, protecting the primary hydroxy group of the intermediate thus formed; reacting this product with a methanephosphonate derivative; and removing the various protecting groups to afford the final product.

The instant process starts with readily available purine and pyrimidine bases, and glycidol. The process offers advantages in economies of both material and labor costs by virtue of eliminating the need for isomer separations and subsequent chromatographic purifications; and unlike prior art processes, the instant process is suitable for large scale synthesis of the final products. Furthermore, the process is stereospecific and, starting with a chiral glycidol, produces the products without racemization.

DETAILED DESCRIPTION OF THE INVENTION

The present process for the preparation of HPMP-type nucleoside antiviral compounds is shown in Scheme I.

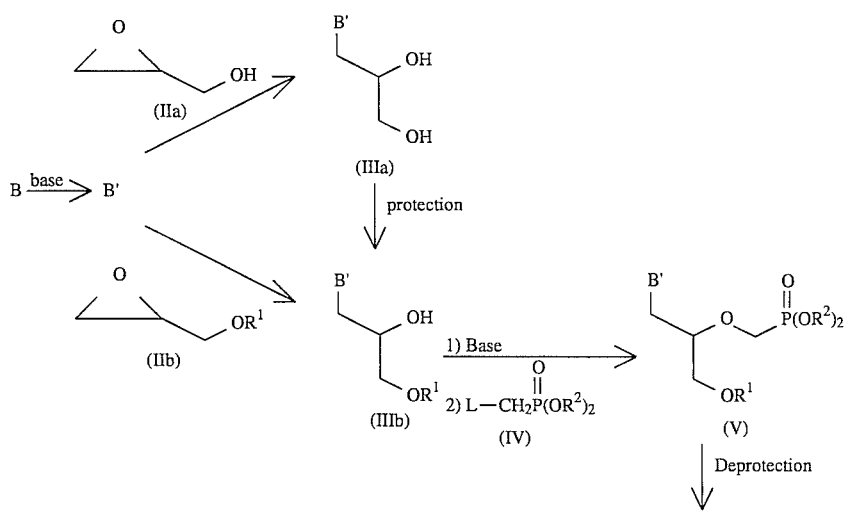

Scheme I (IIa) (IIIa) (IIb) (IIIb) (IV) (V)

-continued
Scheme I

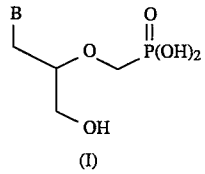
(I)

In Scheme I, B is a purine or a pyrimidine base; B' is a purine or pyrimidine base or a protected purine or pyrimidine base; L is a conventional leaving group; $R^1$ is a hydroxy protecting group; and $R^2$ is an alkyl group having 1–5 carbon atoms.

"Purine or pyrimidine base" includes, but is not limited to, adenine, guanine, thymine, uracil, cytosine, xanthine, hypoxanthine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, 5-ethylcytosine, 5-methylcytosine, 5-bromouracil, 5-iodouracil, 5-ethyluracil, 5-propyluracil, 5-vinyluracil, and 5-bromovinyluracil.

"Protected purine or pyrimidine" refers to a purine or pyrimidine base in which functional groups that may interfere with the desired reaction have been blocked by a group stable under basic conditions. For example, the 4-amino group of cytosine may be blocked by the benzoyl group.

"Leaving group" includes, but is not limited to, halides such as chloride, bromide, and iodide; mesylate; and tosylate. "Alkyl" includes both straight and branched carbon chains. "Hydroxy protecting group" includes, for example, trityl, allyl, and benzyl groups.

In Scheme I, the first step involves the preparation of a compound of formula (IIIb). A purine or a pyrimidine base B' is first treated with a base in order to generate the corresponding anion. The base is not particularly restricted and may be selected from metal hydrides such as sodium and potassium hydrides, metal carbonates such as sodium and potassium carbonates, and metal alkoxides such as potassium t-butoxide; preferably the base is used in a catalytic amount.

Where the purine or pyrimidine base contains 1 or more functional groups that may be reactive to form undesired products under the reaction conditions of the present process, for example, the 4-amino group of cytosine and adenine and the 2-amino and 4-oxo groups of guanine, such functional groups may be blocked using the protecting group commonly employed in nucleoside chemistry. For example, the 4-amino group of adenine and cytosine may be protected by benzoyl; the 4-oxo and 2-amino groups of guanine may be protected by the triphenylmethyl group. The selection of methods for introducing and subsequent removal of such protecting groups are well known to one of ordinary skill in the pertinent art.

The anion B'– generated in situ is reacted with glycidol (IIa) to generate the 2,3-dihydroxy nucleoside of formula (IIIa). The primary alcohol of the compound of formula (IIIa) is blocked prior to the addition of the phosphonate group. For the present process, however, it is preferred that the glycidol reactant is one in which the primary alcohol is protected, i.e. a compound of formula (IIb). The reaction of a protected glycidol with B' consistently gives the corresponding product of formula (IIIb) in higher yields than reactions in which unprotected glycidol is used. The hydroxy protecting group may be, for example, triphenylmethyl-type where the phenyl groups are unsubstituted or 1 or more of the phenyl groups are substituted, for example with methoxy; or allyl, benzyl, and the like. Preferably, the hydroxy protecting group is one selected from the group of triphenylmethyl type compounds.

The reaction is carried out in an inert dipolar aprotic organic solvent such as dimethylformamide, N-methyl-2-pyrrolidinone (NMPO), dimethyl sulfoxide, and hexamethyl phosphoramide at a temperature that favors the formation of the desired products; generally, the reaction temperature is elevated and may be from about 50° C. to about 150° C. Preferably, the reaction is carried out at about 100° C. to about 120° C. The starting materials B' and the glycidol are used in molar equivalent or one or the other reactant may be used in a slight excess, e.g., up to about 2 equivalents relative to the other. Preferably, B' is employed in excess in an amount up to about 1.3 equivalent of the glycidol.

The second step of the present process involves the introduction of the methanephosphonate moiety to the secondary hydroxy group of a compound of formula (IIIb). Prior to carrying out this step, if B' contains an unprotected functional group, this may be optionally protected. For example, the 4-amino group of cytosine may be converted to the corresponding dimethylformamidino derivative upon treatment with N,N-dimethylformamide or an acetal thereof.

Thus, a compound of formula (IIIb) is first treated with a base to generate the corresponding alkoxide anion. The base may be a metal hydride, for example sodium hydride, potassium hydride or lithium hydride; and metal alkoxides, for example, potassium t-butoxide or sodium methoxide and the like. The reaction mixture containing the alkoxide anion is then treated with the methanephosphonate $LCH_2P(O)(OR^2)_2$ (IV) wherein L is a leaving group and $R^2$ is an alkyl group containing 1–5 carbon atoms as previously defined to provide the protected HPMP nucleoside of formula (V). L is preferably selected from the group consisting of p-toluenesulfonate (tosylate), methanesulfonate (mesylate), and trifluoromethanesulfonate (triflate); and $R^2$ is preferably an alkyl group having from 1–3 carbon atoms, e.g., methyl, ethyl, n-propyl, and isopropyl.

The third step of the process involves the removal of the phosphonic protecting group, i e $R^2$ the hydroxy protecting group, and if present, any protecting groups on the purine or pyrimidine base. The phosphonate may be converted to the parent acid by treatment with a trialkylsilyl halide such as trimethylsilyl bromide or trimethylsilyl iodide, and optionally followed by the addition of water. Methods to be employed for the removal of the hydroxy protecting group, and if present, protecting groups on the purine or pyrimidine base will of course depend on the nature of the protecting group; examples of typical deprotecting techniques include acid or base catalyzed hydrolysis, hydrogenation, or metal mediated deprotection.

In a preferred embodiment of the present process, the reaction sequence is conveniently carried out from the starting material to the end product without isolating and purifying the intermediate compounds formed. The elimination of the need for costly and labor intensive isolation and purification of intermediates represent a marked improvement over prior processes. Another advantage of the present invention is that the stereochemistry of the glycidol reactant is maintained throughout the process such that end product having the desired stereo configuration is obtained without racemization.

The process of the present invention, while adaptable to the synthesis of a wide variety of HPMP substituted purine and pyrimidine bases, is especially applicable to the synthesis of hydroxyphosphonomethoxypropyl cytosine (HPMPC); particularly (S)-HPMPC. A preferred embodiment of the present process suitable for the preparation of (S)-HPMPC is illustrated in Scheme II.

tained at the elevated temperature to effect the formation of (S)-N⁴-benzoyl-N¹-[(2-hydroxy-3-triphenylmethyl)propyl]-cytosine (VII).

The above obtained diprotected (2,3-dihydroxy)propyl cytosine is treated with a metal hydride, e.g. sodium hydride, at ice bath temperature, and then treated with diethyl tosyloxymethylphosphonate to provide the compound (S)-N⁴-benzoyl-N¹-[[(2-diethylphosphonylmethoxy)-3-triphenylmethyl]propyl]cytosine (VIII).

Next, the trityl protecting group is removed to provide the compound of formula (IX) by treating the above obtained compound (VIII) with an acidic medium, for example with hydrochloric acid at about 0°–5° C. A wide range of other acids may be employed to accomplish this step, and examples include, acetic acid, formic acid, trifluoroacetic acid, zinc bromide, acidic ion exchange resins, to name but a few. Suitable reaction temperature, and time may be readily ascertained by a person skilled in the art.

Scheme II

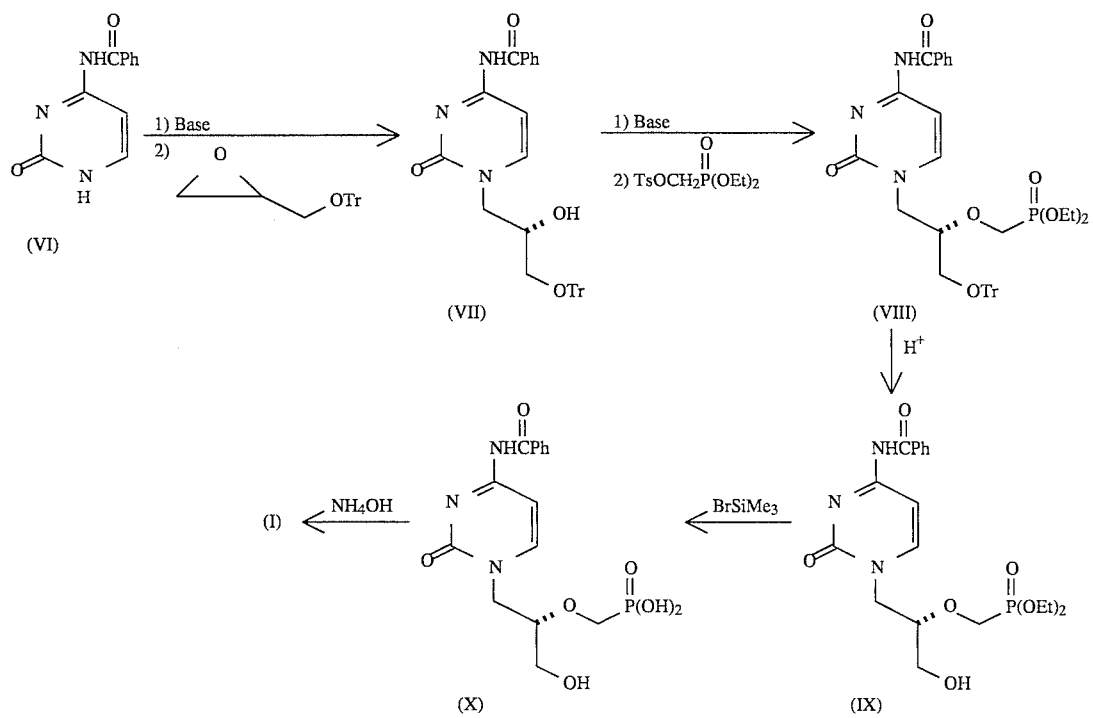

In Scheme II, Tr is triphenylmethyl and Ts is tosyl. N⁴-Benzoylcytosine (VI) is converted to its anionic form by treatment with a base in an aprotic polar organic solvent at elevated temperature; suitable bases are for example sodium hydride, potassium t-butoxide, potassium or sodium carbonate, and the like; suitable solvents are for example dimethylformamide, N-methyl-2-pyrrolidinone, dimethyl sulfoxide, hexamethylphosphoramide, and the like; and typical reaction temperature ranges from about 70° C. to about 150° C. Subsequently, (S)-[(triphenylmethoxy)methyl]oxirane is added to the above reaction solution and the solution main- Following detritylation, the resulting compound (X) is treated with a trialkylsilyl halide such as trimethylsilyl bromide at room temperature to convert the diethyl phosphonate to the phosphonic acid. This latter compound is then treated with a base such as ammonium hydroxide to remove the benzoyl protecting group to afford the desired end product (S)-HPMPC.

Another preferred process for the preparation of (S)-HPMPC is illustrated in Scheme III.

Scheme III

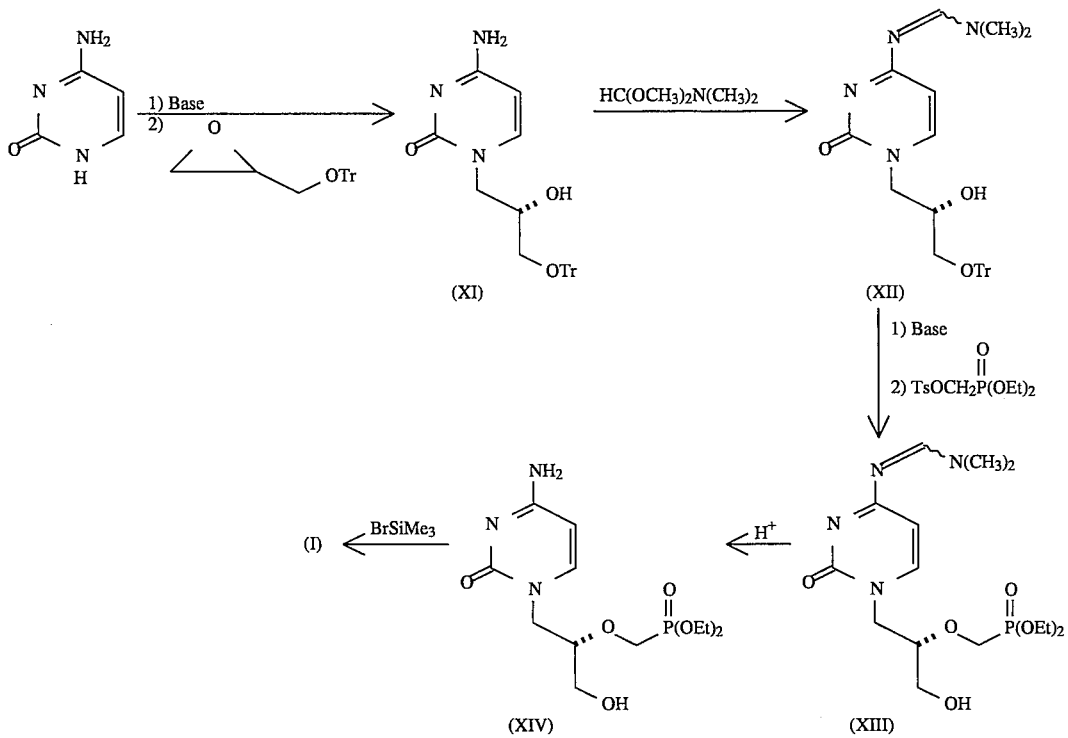

In Scheme III, cytosine is coupled with (S)-(triphenylmethoxy)methyl]oxirane in the presence of a base such as one previously enumerated to give cytosine derivative of formula (XI). The 4-amino group of compound (XI) is then converted to the corresponding dimethyl formamidine derivative (XII) upon treatment with dimethylformamide or an acetal thereof. Compound (XII) is subjected to base promoted alkylation with diethyl tosyloxymethylphosphonate as previously described to provide compound of formula (XIII). Compound (XIII) is deprotected in a acidic medium and the product thereof is treated with e.g. trimethylsilyl bromide to afford (S)-HPMPC. In another preferred process for the preparation of (S)-HPMPC, as illustrated in Scheme IV, cytosine derivative of formula (XI) is treated with a base, followed by diethyl tosyloxymethylphosphonete to afford the compound of formula (XV). The latter compound is treated with an acid to remove the trityl protecting group and affords the compound of formula (XIV) which is converted to (S)-HPMPC as previously described.

Scheme IV

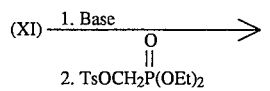

-continued
Scheme IV

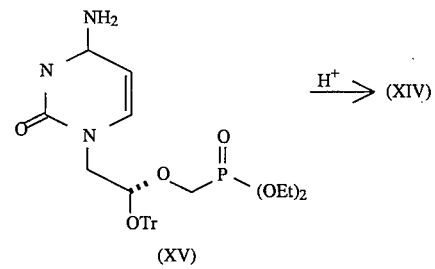

Another aspect of the present invention concerns novel intermediates in the synthesis of (S)-HPMPC. These include compounds of formulas (VII), (VIII), (IX), (X), (XII), (XIII), and (XV).

The process of this invention is illustrated in greater detail by the following examples which are not to be construed to limit the scope of the invention in any manner.

Preparation I. (±)-Triphenylmethoxymethyloxirane

Trityl chloride (18.816 g, 0.067 mol) was added to a stirred solution of (±)-glycidol (5 g, 0.067 mol) and triethylamine (13.84 g, 0.137 mol) in anhydrous methylene chloride (54 ml). After 15 hours of stirring at room temperature, the reaction solution was washed with water (2×10 ml) and brine (20 ml). The organic phase was evaporated after drying over anhydrous $Na_2SO_4$ to give a yellow foam which was purified on silica gel (5% EtOAc in hexane) to afford the title compound (17.64 g, 82.6%) as a solid. $^1H$ NMR ($CDCl_3$): 2.62 (dd, J=2.4 and 5.2 Hz, 1H), 2.77 (t, J=4.5 Hz, 1H), 3.08–3.18 (m, 2H), 3.29–3.80 (m, 1H), 7.20–7.38 (m, 3H), 7.45–7.52 (m, 2H).

Preparation II. (S)-Triphenylmethoxymethyloxirane

A 5 L 3-neck round bottom flask was charged with trityl chloride (133.8 g, 0.48 mol) and methylene chloride (400 ml). It was cooled to 0° C. under $N_2$ and treated with triethylamine (70.7 g, 0.70 mol). After an hour of stirring at 0° C., a solution of (R)-glycidol (88% ee, 37.03 g, 0.5 mol) in methylene chloride (100 ml) was added over 0.75 hour. The resulting solution was allowed to warm to ambient temperature and was stirred for 3 hours. It was then filtered, and the filtrate was washed with water (2×500 ml) and brine (2×500 ml). The organic phase was dried over $MgSO_4$ and concentrated to a foam, which on crystallization from isopropyl alcohol gave the title compound (116.2 g, 76.5%) as an off-white powder.

$[\alpha]_D=-6.01$ (C=1, MeOH).

EXAMPLE 1

Preparation of $(\pm)$-$N^1$-[(2,3-dihydroxy)propyl]cytosine

Cytosine (0.55 g, 4.95 mmol), (±)-glycidol (0.404 g, 5.45 mmol), and anhydrous potassium carbonate (5 mg, 0.04 mmol) in dry DMF (6 ml) were stirred at 71° C. for 3 hours. Glycidol (4) was totally reacted according to TLC of the reaction mixture. The DMF was distilled off under high vacuum, and the resulting yellowish thick liquid was absorbed on silica gel (3 g). This was placed on top of a silica gel column, which was eluted with 20% MeOH in ethyl acetate to give a mixture (0.540 g) of the title compound and a polymer derived from glycidol. Crystallization from ethanol afforded the title compound (0.44 g, 52.3%) as a solid. MP: 169°—71° C. UV: $\lambda_{max}$274 nm ($\epsilon$=8,083). $^1$H NMR (DMSO-$d_6$): 3.11–3.47 (m, 3H), 3.55–3.75 (m, 1H), 3.88 (dd, J=3.3 and 13.3 Hz, 1H), 4.71 (t, J=5.8 Hz, 1H), 4.95 (d, J=5.3 Hz, 1H), 5.61 (d, J=7.1 Hz, 1H), 7.00 (bd, J=23.7 Hz, 2H) , 7.44 (d, J=7.1 Hz, 1H) .

Analysis calcd. for $C_7H_{11}N_3O_3$. $0.5H_2O$: C, 43.30; H, 6.23; N, 21.63 Found: C, 43.33; H, 5.92; N, 21.38

EXAMPLE 2

Preparation of (S)-N1-[(2,3-dihydroxy)propyl]cytosine

Reaction of cytosine (2.2 g, 19.8 mmol) with (R)-glycidol (88% ee, 1.51 ml, 22.8 mmol) in the presence of anhydrous potassium carbonate (40 mg, 0.289 mmol) in dry DMF (20 ml) at 72° C. for 5 hours, as described in Example 1, furnished the title compound (88% ee) in 43.1% yield.

EXAMPLE 3

Preparation of $(\pm)$-$N^1$-[(2-hydroxy-3-triphenylmethoxy)propyl]cytosine by tritylation of $(\pm)$-$N^1$-[(2,3-dihydroxy)propyl]cytosine (a) using 1.1 eq. of glycidol A mixture of cytosine (0.55 g, 4.95 mmol), (±)-glycidol (0.362 ml, 5.46 mol), and anhydrous potassium carbonate (5 mg) in dry DMF (5 ml) was stirred at 71° C. for 3 hours. It was cooled to room temperature and treated with DMAP (0,031 g, 0.25 mmol), dry pyridine (0.783 g, 9.9 mmol), and trityl chloride (1.48 g, 5.2 mmol). The resulting reaction mixture was stirred at 80° C. for 3 hours and at room temperature for 17 hours. It was diluted with ethyl acetate (60 ml), washed with saturated sodium bicarbonate (2×15 ml), water (15 ml), and brine (15 ml), and dried over $MgSO_4$. The ethyl acetate was evaporated to give a crispy foam (1.98 g), and purification by chromatography over silica gel (10–15% methanol in ethyl acetate) furnished the title compound as a crystalline solid (0.74 g, 35%). MP: 227°–228° C. UV: $\lambda_{max}$274 nm ($\epsilon$=7,149). $^1$H NMR (DMSO-$d_6$): 2.81–2.98 (m, 2H), 3.26–3.42 (m, 1H), 3.85–3.97 (m, 1H), 4.02 (dd, J=4.7 and 14.2 Hz, 1H), 5.23 (d, J=5.8 Hz, 1H), 5.54 (d, J=7.1 Hz, 1H), 7.93 (bd, 2H), 7.1–7.29 (m, 16H).

(b) using 1.5 e.g. of glycidol

Cytosine (0.275 g, 2.48 mmol), (±)-glycidol (0,281 g, 3.7 mmol), and anhydrous potassium carbonate (2.5 mg, 0,018 mmol) in dry DMF (2.5 ml) were stirred at 70° C. for 1.5 hours. The DMF was distilled under reduced pressure. PMR of the resulting solid showed that it contained $(\pm)$-$N^1$-[(2,3-dihydroxy)propyl]cytosine and cytosine in 89:11 ratio.

The above solid was dissolved in dry pyridine (4 ml) and trityl chloride (0.602 g, 2.14 mmol) and DMAP (13 mg) were added successively at room temperature. After 3 hours of stirring at 85° C. followed by work-up as described in Example 3 (a), supra, a foamy solid (0.88 g) was obtained. Crystallization from methylene chloride and toluene gave the title compound (0.360 g 34%). The mother liquor was concentrated and purified by silica gel chromatography (10% methanol in ethyl acetate) to give the title compound (60 mg, 5.7%) and $(\pm)$-$N^1$-[[2-[(2-hydroxy-3-triphenylmethoxy)propyloxy]-3-triphenylmethoxy]propyl]cytosine (hereinafter referred to as the dimer) (10 mg, 0.8%).

(c) using 2 eq. of glycidol

The above experiment was repeated using 2 eq. of (±)-glycidol to provide the title compound in 39.6% yield and the dimer in 1.6% yield.

EXAMPLE 4

Preparation of $(\pm)$-$N^1$-[(2-hydroxy-3-triphenylmethoxy)propyl]cytosine by reaction of cytosine and (±)-triphenylmethoxymethyloxirane (a) using a catalytic amount of NaH Cytosine (80 mg, 0.72 mmol) was added to a stirred suspension of 80% NaH (4 mg, 0.13 mmol) in dry DMF (3 ml). After an hour at room temperature, (±)-trityloxymethyloxirane (0.19 g, 0.6 mmol) was added to the reaction mixture, and stirring continued at 106° C. for 5 hours. The reaction was completed as indicated by TLC of the reaction mixture. It was cooled, and the DMF was distilled off under vacuum. The resulting solid was partitioned between ethyl acetate (20 ml) and water (2 ml). The organic phase was separated, washed once again with water (5 ml), and dried over $Na_2SO_4$. Evaporation of the ethyl acetate gave the brown solid (0.28 g) which was crystallized from methylene chloride-toluene (2 ml and 30 ml) to furnish the title compound (0.21 g) in 81.7% yield.

(b) using one equivalent of NaH

Carrying out the above reaction using (±)-trityloxymethyloxirane (0.190 g, 0.6 mmol), cytosine (67 mg, 0 6 mmol), and sodium hydride (80% 18 mg 0 6 mmol) in anhydrous DMF (4 ml) furnished the title compound (60 mg) in 23.3% yield.

c. using $K_2CO_3$ instead of NaH

Following the procedure described above, the title compound was obtained in 82% yield from (±)-trityloxymethyloxirane (0.19 g, 0.6 mmol) and cytosine (0.08 g, 0.72 mmol) in the presence of potassium carbonate (10 mg, 0.072 mmol) in anhydrous DMF (3 ml).

EXAMPLE 5

Preparation of $(\pm)$-$N^4$-benzoyl-$N^1$-[(2-hydroxy-3-triphenylmethoxy)propyl]cytosine (a) using 1 equivalent of $N^4$-benzoylcytosine Treatment of $N^4$-benzoylcytosine (0.388 g, 1.803 mmol) with (±)-trityloxymethyloxirane (0.571 g, 1.805 mmol) in the presence of 80% sodium hydride (12 mg, 0.4 mmol), according to the procedure of Example 4 (a), gave the title compound as a crystalline solid in 72.9% yield after chromatography over silica gel using hexane-EtOAc (1:3). MP: 105°–7° C. UV: $\lambda_{max}$259 nm ($\epsilon$=23,500), 306 nm ($\epsilon$=10, 380). $^1$H NMR (CDCl$_3$): 3.05–3.18 (m, 1H), 3.21–3.33 (m, 1H), 3.66–3.90 (m, 1H), 4.2 (bS, 1H), 4.35 (d, J=13.6 Hz, 1H), 7.13–7.72 (m, 15H), 7.88 (d, J=7.5 Hz, 1H), 8.73 (bS, 1H).

Analysis calcd. for C$_{33}$H$_{29}$N$_3$O$_4$: C, 74.56; H, 5.50; N, 7.90 Found: C, 74.02; H, 5.67; N, 7.63

(b) using 1.2 equivalents of N$^4$-benzoylcytosine (±)-Trityloxymethyloxirane (0.762 g, 2.41 mmol) was reacted with N$^4$-benzoylcytosine (0.621 g, 2.89 mmol) in the presence of 80% sodium hydride (16 mg, 0.53 mmol) in dry DMF, as described above, to obtain the title compound in 85% yield.

EXAMPLE 6

Preparation of (S)-N$^4$-benzoyl-N$^1$-[(3-allyloxy-2-hydroxy)propyl]cytosine

To sodium hydride (80%, 12 mg, 0.4 mmol) stirring in anhydrous DMF (4.5 ml) at room temperature was added N$^4$-benzoylcytosine (0.466 g, 2.17 mmol). The reaction mixture was stirred for an hour and treated with (S)-allyloxymethyloxirane (0.206 g, 1.8 mmol). It was then heated at 105° C. for 6 hours, cooled, and concentrated in vacuo. The resulting orange red gummy material was treated with water (5 ml) and ethyl acetate (20 ml). It was stirred for 5 minutes, and the insoluble solid (0.145 g, 31.1% of recovery) was collected by filtration and identified as N$^4$-benzoylcytosine. The filtrate was transferred into a separatory funnel, and the ethyl acetate layer was separated. It was washed with water (3×5 ml), dried over Na$_2$SO$_4$, and evaporated to obtain 0.423 g of pale-yellow solid. Slurrying of this material in diethyl ether gave the title compound (0.331 g) in 55.7% yield. The ether filtrate was evaporated, and the resulting light greenish gummy material was purified by flash chromatography on silica gel (0–5% MeOH in EtOAc) to furnish the title compound (20 mg) in 3.6% yield. MP: 139°–41° C. [α]$_D$=−55.06 (C=1.155, MeOH). UV: $\lambda_{max}$259 nm ($\epsilon$=21,500), 305 nm ($\epsilon$=10,120). $^1$H NMR (CDCl$_3$): 3.4–3.56 (m, 2H), 3.77 (dd, J=7.6 and 13.5 Hz, 1H), 3.98 (d, J=5.7 Hz, 3H), 4.16–4.25 (m, 1H), 4.28 (dd, J=2.7 and 13.5 Hz, 1H), 5.10–5.25 (m, 2H), 5.79–5.92 (m, 1H), 7.39–7.62 (m, 4H).

Analysis calcd. for C$_{17}$H$_{19}$N$_3$O$_4$: C, 61.97; H, 5.85; N, 12.79 Found: C, 61.82; H, 6.05; N, 12.77

EXAMPLE 7

Preparation of (±)-N$^4$-benzoyl-N$^1$-[(3-allyloxy-2-hydroxy)propyl]cytosine

The title compound was prepared in 39.5% yield, following the procedure of Example 6, from (±)-allyloxymethyloxirane (9.02 g, 0.079 mol), N$^4$-benzoylcytosine (20.40 g, 0.095 mol), and 80% sodium hydride (0.526 g, 0.018 mol) in dry DMF (241 ml).

EXAMPLE 8

Preparation of (S)-N$^4$-benzoyl-N$^1$-[(3-benzyloxy-2-hydroxy)propyl]cytosine (R)-benzyloxymethyloxirane (0.296 g, 1.8 mmol) in dry DMF (0.5 ml) was added to sodium salt of N$^4$-benzoylcytosine, prepared from N$^4$-benzoylcytosine (0.388 g, 1.8 mmol) and 80% sodium hydride (0.012 g, 0.4 mmol) in dry DMF (4 ml) at room temperature for an hour, and stirred at 110° C. for 6 hours. The reaction was complete as confirmed by HPLC of the reaction. Most of the DMF was distilled off under reduced pressure. The resulting gummy product was partitioned between ethyl acetate (20 ml) and water (5 ml). The ethyl acetate layer was separated, washed with water (3×10 ml), dried over Na$_2$SO$_4$, and evaporated to give a yellow product (0.595 g). Trituration with ethyl acetate furnished the title compound (0.392 g) in 57.3% yield. The mother liquor was concentrated and chromatographed on silica gel (ethyl acetate) to give the title compound (50 mg, 7.3%). MP: 138° C. [α]$_D$=−49.19 (C=1.425, MeOH). UV: $\lambda_{max}$ 259 nm ($\epsilon$=22,440), 306 nm ($\epsilon$=10,220). $^1$H NMR (CDCl$_3$): 3.45–3.58 (m, 3H), 3.79 (dd, J=7.1 and 13.3 Hz, 2H), 4.16–4.33 (m, 2H), 4.51 (s, 2H), 7.2–7.6 (m, 8H), 7.69 (d, J=7.2 Hz, 1H), 7.89 (d, J=7.4 Hz, 2H), 8.91 (bS, 1H).

Analysis calcd. for C$_{21}$H$_{21}$N$^3$O$_4$·0.9H$_2$O: C, 63.76; H, 5.81; N, 10.62 Found: C, 63.97; H, 5.50; N, 10.63

Example 9

Preparation of (±)-N$^4$-benzoyl-N$^1$-[(3-benzyloxy-2-hydroxy)propyl]cytosine

Treatment of (±)-benzyloxymethyloxirane (6.0 g, 0.0365 mol) with N$^4$-benzoylcytosine (9.446 g, 0.0439 mol) in the presence of sodium hydride (80% pure, 0.263 g, 8.1 mmol) in dry DMF (85 ml), according to the procedure of Example 8, afforded the title compound (8.2 g) in 59.2% yield. MP: 144°–6° C.

EXAMPLE 10.

Preparation of (±)-N$^1$-[(2-diethylphosphonylmethoxy-2-triphenylmethoxy)propyl]cytosine One Pot Synthesis: A mixture of cytosine (0,134 g, 1.21 mmol) and 80% sodium hydride (8 mg, 0.27 mmol) in anhydrous DMF (3 ml) was stirred at room temperature. After 1 hour, (±)-trityloxymethyloxirane (0.38 g, 1.2 mmol) was added in 1 portion, and stirring was continued for 5 hours at 105° C. The formation of (±)-N$^1$-[(2-hydroxy-3-trityloxy)propyl] cytosine was noted by its HPLC.

The above homogenous reaction solution was cooled in an ice bath and successively treated with 80% sodium hydride (0.100 g, 3.3 mmol) and diethyl tosyloxymethylphosphonate (85% pure, 0.682 g, 1.8 mmol). After being stirred at 0° C. for 0.5 hour and at room temperature for 15 hours, a few drops of ethanol were added to quench excess sodium hydride. The solvent was removed under reduced pressure, and the resulting orange residue was partitioned between ethyl acetate (30 ml) and water (5 ml). The organic phase was separated and washed with saturated sodium bicarbonate (10 ml) and brine (10 ml). After drying over Na$_2$SO$_4$, the ethyl acetate was evaporated to give the orange-colored product (0.550 g), which was purified by chromatography on silica gel (10–15% MeOH in CH$_2$Cl$_2$) to furnish the title compound (0.26 g, 37.4%) as a foamy solid. $^1$H NMR (CDCl$_3$): 1.25 (t, J=7 Hz, 6H), 2.97–3.12 (m, 1H), 3.33 (dd, J=3 and 10.5 Hz, 1H), 3.55–3.68 (m, 2H), 3.84–3.96 (m, 2H), 3.96–4.24 (m, 5H), 5.63 (d, J=6.9 Hz, 1H), 7.0–7.6 (m, 18H).

EXAMPLE 11

Preparation of (±)-N$^1$-[(2-dimethylphosphonylmethoxy-3-triphenylmethoxy)propyl]cytosine Repeating the experiment of Example 10, using dimethyl tosyloxymethylphosphonate instead of diethylphosphonate afforded the title compound in 15.6% yield. $^1$H NMR (CDCl$_3$): 3.0–3.1 (m, 1H), 3.27 (dd, J=2.8 and 10.5 Hz, 1H), 3.51–4.26 (m, 10H), 4.17 (dd, J=3.0 and 13.6 Hz, 1H), 5.69 (d, J=6.9 Hz, 1H), 7.0–7.66 (m, 18H).

EXAMPLE 12

Preparation of (±)-N$^1$-[(2-diethylphosphonylmethoxy- 3-hydroxy)propyl]cytosine Treatment of cytosine (0.249 g, 2.24 mmol) with (±)-trityloxymethyloxirane (0.590 g, 1.87 mmol) in the presence of a catalytic amount of 80% sodium hydride (13 mg, 0.44 mmol) followed by in situ alkylation of the intermediate with diethyl tosyloxymethylphosphonate (85.1% pure, 1.06 g, 2.80 mmol) in the presence of 80% sodium hydride (0.099 g, 3.3 mmol), according to the procedure of Example 10, gave the crude (±)-N$^1$-[(2-diethylphosphonylmethoxy-3-trityloxy)propyl] cytosine (1.267 g).

To the above nucleotide, 80% acetic acid (20 ml) was added and stirred at 95° C. for 3 hours. Water (20 ml) was added to the reaction which was then cooled to –0° C. The precipitated trityl alcohol was collected by filtration. The filtrate was evaporated, and the resulting thick product was co-distilled with water (3×30 ml) and with toluene (3×30 ml) to remove acetic acid. It was then applied on a silica gel column which, on elution with 15% MeOH in CH$_2$Cl$_2$, afforded the title compound (0.147 g, 23.5%) as a gummy material. Further elution of the column with 20% MeOH in CH$_2$Cl$_2$ gave (±)-N$^1$-[(2,3-dihydroxy)propyl]cytosine (20.2 mg, 6%). $^1$H NMR (MeOH-d$_4$): 1.30 (t, J=7.1 Hz, 3H), 1.31 (t, J=7.1 Hz, 3H), 3.5–3.63 (m, 1H), 3.67–3.92 (m, 4H), 3.97–4.22 (m, 6H), 5.85 (d, J=7.2 Hz, 1H), 7.53 (d, J=7.2 Hz, 1H).

EXAMPLE 13

Preparation of (±)-N$^1$-[(2-diethylphosphonylmethoxy- 3-hydroxy)propyl]cytosine via formamidine method A mixture of the sodium salt of cytosine, obtained from cytosine (0.134 g, 1.21 mol) and 80% sodium hydride (8 mg, 0.27 mmol) in dry DMF (3 ml) at room temperature for 1 hour, and (±)-trityloxymethyloxirane (0.38 g, 1.2 mmol) was stirred at 110° C. for 5 hours. The resulting solution of 12 was cooled to room temperature, and DMF dimethyl acetal (0.286 g, 2.4 mmol) was added in 1 portion. It was then stirred at 85° C. for 1.5 hours and concentrated under reduced pressure to ca. 1 ml of the crude dimethylformamidine derivative of 11. This and diethyl tosyloxymethylphosphonate (0.909 g, 2.4 mmol) in anhydrous DMF (3 ml) was cooled to 0° C. and treated with 80% sodium hydride (64 mg, 2.13 mmol). The resulting yellow reaction mixture was stirred at 0° C. for 1.5 hours and at room temperature for 14 hours. The crude product obtained after work-up is a mixture of (±)-N'-[(2-diethylphosphonylmethoxy-3-trityloxy)propy] cytosine and its N$^4$-dimethylformamidine derivative. This mixture was dissolved in 80% acetic acid (11 ml) and refluxed for 3 hours. After work-up, the yellowish gummy product (0.693 g) was obtained which, on purification by chromatography on silica gel (15% MeOH in EtOAc), afforded the title compound (0.175 g) in 43.6% yield.

EXAMPLE 14

Preparation of (±)-N$^1$-[(2-ethylhydrogenphosphonylmethoxy- 3-hydroxy)propyl]cytosine 2N Sodium hydroxide solution (4.5 ml) was added to (±)-N$^1$-[(2-diethylphosphonylmethoxy-3-hydroxy)propyl] cytosine (0.230 g, 0.69 mmol). TLC of the reaction after 1.25 hours at room temperature showed that starting material was completely consumed. The reaction was acidified with Dowex 50×8 (H$^+$) and filtered. The resin was washed with 20 ml of water. The combined filtrate was evaporated to provide the title compound (0.163 g) in 77.3% yield. $^1$H NMR (D$_2$O): 1.26 (t, J=7.1 Hz, 3H) , 2.52–2.68 (m, 2H), 3.75–4.0 (m, 6H), 4.21 (dd, J=2.8 and 14.1 Hz, 1H), 6.19 (d, J=7.6 Hz, 1H), 7.88 (d, J=7.6 Hz, 1H). MS: molecular ion (m/e) for C$_{10}$H$_{18}$N$_3$O$_6$P,308.1011: Found: 308. 1009

EXAMPLE 15

Preparation of (S)-N$^4$-benzoyl-N$^1$-[(2-hydroxy-3-triphenylmethoxy)propyl] cytosine (a) To N$^4$-benzoylcytosine (100.1 g, 0.47 mol) in dry DMF (1,000 ml) at 100° C. under N$_2$ was added 80% sodium hydride (3.0 g, 0.10 mol) in 1 portion, and the slurry was stirred for 0.25 hour. (S)-trityloxymethyloxirane (88% ee, 125.1 g, 0.40 mol) was added and further stirred at 110° C. for 4 hours. The reaction was completed as confirmed by its HPLC. The reaction mixture was filtered and used in the subsequent reaction without further purification. The filtrate contained a 90% in solution yield of the title compound based on HPLC.

(b) In a separate experiment, the crude product obtained from the above reaction was purified by chromatography on silica gel (3–5% MeOH in CH$_2$Cl$_2$) and provided analytically pure title compound. MP: 105°–7° C. UV: $\lambda_{max}$ 259 nm ($\epsilon$=23,500), 306 nm ($\epsilon$=10,380). $^1$H NMR (CDCl$_3$): 3.05–3.18 (m, 1H), 3.21–3.33 (m, 1H), 3.66–3.90 (m, 1H), 4.2 (bS, 1H), 4.35 (d, J=13.6 Hz, 1H), 7.13–7.72 (m, 15H), 7.88 (d, J=7.5 Hz, 1H), 8.73 (bS, 1H).

Analysis calcd. for C$_{33}$H$_{29}$N$_3$O$_4$: C, 74.56; H, 5.50; N, 7.90 Found: C, 74.02; H, 5.67; N, 7.63

(c) The reaction described in (a) supra was also repeated using solvents and conditions to afford the title compound.
  (1) NaH, NMPO, 70°–80° C. for 2 hours followed by 100°–104° for 3.5 hours.
  (2) NaH, 18-crown-6, DMF, 103° C., 5 hours.
  (3) NaH, benzyltriethylammonium chloride, DMF, 70° C. for 6 hours, 105° C. for 4 hours.
  (4) KOC(CH$_3$)$_3$, DMF, 70° C. for 16 hours followed by 105° C. for 8 hours.

EXAMPLE 16

Preparation of (S)-N$^4$-benzoyl-[(diethylposphonylmethoxy-3-triphenylmethoxy)propyl]-cytosine (a) A solution of the crude (S)-N$^4$-benzoyl-N$^1$-[(2-hydroxy- 3-triphenylmethoxy)propyl]cytosine in DMF, obtained in Example 15 (a), was placed in a 5 L 3-neck round bottom flask and cooled to 0° C. 80% sodium hydride (32.4 g, 1.06 mol) was added in 2 portions, and an exotherm of 8° C. was noted. Immediately, diethyl tosyloxymethylphosphonate (80%. pure, 215.6 g, 0.54 mol) was added, and the reaction was completed after 6 hours of stirring. The reaction was diluted with ethyl acetate (2 L), quenched with water, washed with water (2×1 L) and saturated NaHCO$_3$ (1 L), dried over MgSO$_4$, and concentrated to afford crude title compound (230.1 g) with 2% of (S)-trityloxymethyloxirane, as indicated by its proton NMR spectrum. This crude product was used in the next procedure without further purification.

(b) In a separate experiment, a small amount of the crude product was purified by column chromatography on silica gel (1–3% MeOH in CH$_2$Cl$_2$) to provide an analytical sample of the title compound. $^1$H NMR (DMSO-d$_6$): 1.14 (t, J=7 Hz, 3H), 1.16 (t, J=7 Hz, 3H), 2.94–2.98 (m, 1H), 3.24–3.31 (m, 1H), 3.58–4.09 (m, 9H), 7.23–7.63 (m, 19H), 7.98 (d, J=7 Hz, 3H), 11.19 (bS, 1H).

Analysis calcd. for $C_{38}H_{40}N^3O_7P \cdot 0.5H_2O$: C, 66.07; H, 5.98; N, 6.08 Found: C, 65.96; H, 5.84; N, 6.09

EXAMPLE 17

Preparation of (S)-$N^4$-benzoyl-$N^1$-[(2-diethylphosphonylmethoxy-3-hydroxy)propyl]cytosine (a) Hydrogen chloride gas was bubbled into a solution of the crude (S)-$N^4$-benzoyl-$N^1$-[(2-diethylphosphonyl-3-triphenylmethoxy)propyl] cytosine (230.1 g, obtained from Example 16) in methylene chloride (1.2 L) at 0°–5° C. until starting material was consumed as determined by HPLC (ca 10 minutes). Water (500 ml) was added, and the resulting 2-phase mixture stirred rigorously for 5 minutes. The organic phase was separated and extracted with 10% hydrochloric acid (2×250 ml). The combined aqueous solution was cooled to 0°–5° C., adjusted to pH=8 with 40% sodium hydroxide solution, and then extracted with $CH_2Cl_2$ (2×500 ml). The combined $CH_2CL_2$ solution was dried over $MgSO_4$ and concentrated in vacuo to give crude title compound (96.2 g), as a viscous oil, in 55% yield from (S)-trityloxymethoxyoxirane after 3 steps. $^1H$ NMR (DMSO-$d_6$): 1.16 (t, J=7 Hz, 3H), 1,18 (t, J=Hz, 3H), 3.44–3.57 (m, 2H), 3.68–3.80 (m, 3H), 3.88–4.01 (m, 5H), 4.13 (dd, J=8 and 17 Hz, 1H), 4.88 (t, J=6 Hz, 1H), 7.27 (br d, J=7 Hz, 1H), 7.49 (t, J=7 Hz, 2H), 7.60 (t, J=7 Hz, 1H), 7.98 (d, J=7 Hz, 3H), 11.18 (br s, 1H).

Analysis calcd. for $C_{19}H_{26}N^3O_7P \cdot 0.5H_2O$: C, 50.89; H, 6.07; N, 9.37 Found: C, 50.99; H, 6.03; N, 9.32

(b) Detritylation was carried out with the following reagents and conditions to afford the title compound in moderate to excellent yields:

(1) 80% acetic acid, 75° C., 45 minutes.

(2) 80% acetic acid, 100° C., 30 minutes.

(3) 80% acetic acid, 60° C., 3 hours.

(4) 80% formic acid, 0°–5° C., 30 minutes.

(5) 95–97% formic acid, room temperature, 5 minutes.

(6) Trifluoroacetic acid, n-butanol or isopropyl alcohol, or $CH_2Cl_2$, 22 hours.

(7) $ZnBr_2$, $CH_2Cl_2$, room temperature, 10 minutes-3 hours.

(8) Amberlyst 15 ($H^+$), MeOH, 50° C., 24 minutes.

(9) Amberlyst 15 ($H^+$) activated by HCl/MeOH wash, 50° C., 6.5 hours.

(10) Dowex 50×8 ($H^+$) activated by HCl/MeOH.

EXAMPLE 18

Preparation of (S)-$N^4$-benzoyl-$N^1$-[(3-hydroxy-2-phosphonylmethoxy)propy] cytosine A solution of (S)-$N^1$-[(2-diethylphosphonylmethoxy-3-hydroxy)propyl-$N^4$]-benzoylcytosine (188 g, 0.428 mol) in methylene chloride (1.2 L) at room temperature under argon was treated with bromotrimethylsilane (200 ml, 1.52 mol), and the resulting mixture was stirred for 18 hours. It was then concentrated in vacuo to a residue which was redissolved in methylene chloride (500 ml) and reconcentrated to furnish the crude persilylated title compound (289 g) as a tan foam. This material was used in the next step without further purification. An analytical sample of the title compound was prepared by treating the crude foam with water from which the desired title compound crystallized. $^1H$ NMR (DMSO-$d_6$): 3.45–3.81 (m, 6H), 4.11 (dd, J=4 and 13 Hz, 1H), 7.26 (d, J=7 Hz, 1H), 7.49 (t, J=7 Hz, 2H), 7.61 (t, J=7 Hz, 1H), 7.98 (d, J=7 Hz, 2H), 8.04 (d, J=7 Hz, 1H).

Analysis calcd. for $C_{15}H_{18}N_3O_7P \cdot 0.5H_2O$: C, 45.93; H, 4.84; N, 10.71 Found: C, 46.04; H, 4.67; N, 10.71

EXAMPLE 19

Preparation of (S)-$N^1$-[(3-hydroxy-2-phosphonylmethoxy]propyl] cytosine

The crude persilyated (S)-$N^4$-benzoyl-$N^1$-[(3-hydroxy-2-phosphonylmethoxy)propyl] cytosine (289 g), obtained from the previous example, was dissolved on conc $NH_4OH$ (850 ml) and stirred at room temperature for 4 hours. The aqueous reaction mixture was extracted with $CH_2Cl_2$ (2×600 ml) to remove most of the benzamide and then filtered and concentrated in vacuo until the pH of the aqueous solution was neutral. The concentrated solution was diluted with water to a volume of 800 ml, and ethanol (600 ml) was added. The product was precipitated by adjusting the pH to 3.0 with careful addition of conc HCl (65 ml). The resulting thick slurry was stirred at room temperature for 1 hour and then stored at 0°–5° C. for 16 hours. The solid product was collected by filtration, washed with water ethanol (2:1, 2×150 ml), and dried to constant weight in vacuo at 40° C. to give (S)-HPMPC (105 g) in 78% yield from 22S after 2 steps. This material contained 5% of the undesired (R)-isomer as determined by chiral HPLC. Two crystallizations of the crude product by adjusting an aqueous slurry to pH=6 with 40% NaOH solution, followed by reprecipitation with conc HCl to pH=3, reduced the level of the undesired (R)-isomer to 2.4, a 90% weight recovery. MP: 260° C. (decomp). $[\alpha]_D=-86.65$ (C=0.40, $H_2O$). $^1H$ NMR ($D_2O$): d 3.59–3.67 (m, 2H), 3.79–3.94 (m, 4H), 4.20 (dd, J=3 and 14 Hz, 1H), 6.17 (d, J=8 Hz, 1H), 7.90 (d, J=8 Hz, 1H).

Analysis calcd. for $C_8H_{14}N_3O_6 \cdot 2H_2O$: C, 30.48; H, 5.75; N, 13.33 Found: C, 30.30; H, 5.70; N, 13.25

EXAMPLE 20

Preparation of (±)-$N^1$-[(3-hydroxy-2-phosphonylmethoxy]propyl]cytosine

Synthesis of (±)-HPMPC was achieved in 42.4% yield after 5 steps (Examples 15, 16, 17, 18, and 19) starting from (±)-trityloxymethyloxirane and $N^4$-benzoylcytosine.

EXAMPLE 21

Preparation of (R)-$N^1$-[(3-hydroxy-2-phosphonylmethoxy)propyl] cytosine

The title compound (R)-HPMPC was prepared from (S)-glycidol (88% ee) and $N^4$-benzoylcytosine, following the method described for (S)-HPMPC.

EXAMPLE 22

Preparation of (±)-[(3-hydroxy-2-phosphonylomethoxy)propyl] uracil

A solution of (±)-$N^1$-[(2-diethylphosphonyl-3-hydroxy)propyl] cytosine (0.228 g, 0.68 mol) in 2N sodium hydroxide (4.5 ml) was heated at 82° C. for 60 hours. The reaction was complete as indicated by its HPLC. It was acidified with Dowex 50×8 ($H^+$) form at room temperature and filtered, and the resin was washed with water (30 ml). Evaporation of the filtrate afforded the title compound (0.157 g, 82.4%) as a solid. $^1H$ NMR ($D_2O$): 3.16–3.29 (m, 1H), 2.55–4.17 (m, 9H), 5.87 (d, J=7.9 Hz, 1H), 7.72 (d, J=7.9 Hz, 1H).

What is claimed is:

1. A process for preparing a compound of formula (Ia) or (Ib)

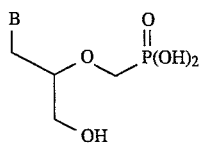

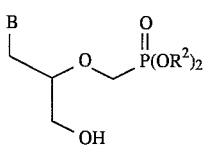

wherein B is a purine or pyrimidine base, which comprises the steps of (a) reacting, in a reaction mixture, B' in the presence of a base with a compound of formula (IIb) to form the intermediate (IIIb)

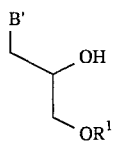

and, without separating intermediate (IIIb) from the reaction mixture, reacting intermediate (IIIb) with a phosphonate of formula (IV)

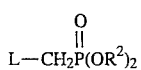

to form an intermediate of formula (V)

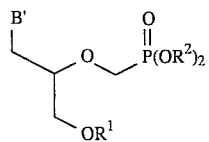

where B' is a purine or pyrimidine base or a suitably protected purine or pyrimidine base, $R^1$ is a hydroxy protecting group, L is a leaving group, and $R^2$ is a phosphonic protecting group selected from alkyl having 1–5 carbon atoms; and (b) replacing the $R^1$ hydroxy protecting group, and optionally, the $R^2$ or B' protecting groups, with hydrogen to form the product of formula (Ia) or (Ib).

2. The process of claim 1 wherein $R^1$ is replaced with hydrogen by treatment with an acidic medium.

3. The process of claim 1 wherein $R^1$ of a compound of formula (IIIb) is triphenylmethyl and $R^2$ is ethyl or isopropyl.

4. The process of claim 1 wherein B' is cytosine or $N^4$-protected cytosine.

5. The process of claim 1 wherein the process is carried out in an inert polar aprotic solvent.

6. The process of claim 1 wherein B' is $N^4$-benzoylcytosine and $R^1$ is triphenylmethyl.

7. The process of claim 1 which further comprises reacting a compound of formula (IIIb) wherein B' is cytosine with dimethylformamide dimethyl acetal to form a compound of formula (XVI)

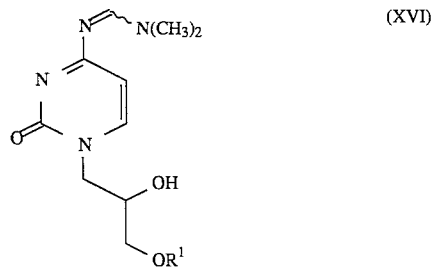

wherein $R^1$ is as defined in claim 1.

8. The process of claim 1 wherein compound (IIb) is (S)-triphenylmethoxymethyloxirane.

9. The process of claim 1 wherein the product is (S)-$N^1$-[3-hydroxy-2-(phosphonylmethoxy)propyl]cytosine.

10. The process of claim 1 wherein the base is a metal hydride or metal alkoxide.

11. The process of claim 10 wherein the base is sodium hydride.

12. The process of claim 5 wherein the solvent is dimethylformamide.

* * * * *